US00PP10492P

United States Patent [19]

Holtkamp, Sr.

[11] Patent Number: Plant 10,492

[45] Date of Patent: Jul. 14, 1998

[54] AFRICAN VIOLET PLANT NAMED ILONA

[75] Inventor: Reinhold Holtkamp, Sr., Rees-Haffen, Germany

[73] Assignee: International Plant Breeding A.G., Bern, Switzerland

[21] Appl. No.: 797,615

[22] Filed: Feb. 7, 1997

[51] Int. Cl.[6] ..... A01H 4/00

[52] U.S. Cl. ..... Plt./69.1

[58] Field of Search ..... Plt./69.1

*Primary Examiner*—James R. Feyrer
*Assistant Examiner*—Melissa L. Kimball
*Attorney, Agent, or Firm*—Foley & Lardner

[57] ABSTRACT

A new and distinct cultivar of African violet named Ilona, as described and illustrated, and particularly characterized by its small, single violet-shaped, multi-colored light pink flowers with bright pink center radiating into the petals and purplish touches in the center; strong, upright flower stems that curve slightly toward the center to form a compact bouquet above the leaves; medium green, oval to spear-shaped leaves; profuse flowering; vigorous and compact growth habit; flowering 9–10 weeks after potting, and by its long lasting and non-dropping flowers.

1 Drawing Sheet

The present invention comprises a new and distinct cultivar of African violet plant, botanically known as *Saintpaulia ionantha*, and hereinafter referred to by the cultivar name Ilona.

The new cultivar was referred to during the breeding and selection process by the designation 920/13 and is a product of a planned breeding program. The new cultivar was originated from a cross made by me in the controlled breeding program in Haffen, Federal Republic of Germany. The female, or seed parent was a cultivar designated 259. The male, or pollen parent was a cultivar designated 920.

Ilona was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Ilona has not been observed under all possible environmental conditions. The phenotype may vary significantly with variations in environment such as temperature, light intensity and day length. The following observations, measurements and values describe the new cultivar as grown in Haffen, West Germany and Nashville, Tenn. under greenhouse conditions which closely approximate those generally used in commercial practice.

The following traits have been repeatedly observed and are determined to be basic characteristics of Ilona, which in combination distinguish this African violet as a new and distinct cultivar:

(1) Strong, upright flower stems curving slightly toward the center.

(2) Small, single violet-shaped, multi-colored flowers which are light pink with a bright pink center radiating into the petals and purplish touches in the center (3) Profuse flowering.

4) Each plant carries 8–10 and more upright flower stems each of which carries 11–13 and more flowers.

(5) Long lasting, non-dropping flowers.

(6) Vigorous and compact grower.

(7) Plant saleable 9 to 10 weeks after potting.

(8) Seed capsules push slightly through.

(9) Medium green, oval to spear-shaped, slightly wavy leaves.

(10) After maturity the flowers dry off, and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Color Chart (R.H.S.), except where general colors of ordinary significance are referred to. Color values were taken under natural sunlight conditions at approximately 12 p.m. in Nashville, Tenn.

Botanical classification: *Saintpaulia ionantha*, Ramat., c.v. Ilona.

Parentage:

*Male parent.*—920.

*Female parent.*—259.

Propagation: The new cultivar holds its distinguishing characteristics through successive propagations by leaf cuttings.

Plant: From 9 cm to 11 cm tall when grown in pots, and 24–27 cm in diameter when fully grown.

*Leaves.*—General form: Oval to spear-shaped. Diameter: 50–60 mm wide and 65–75 mm long. Texture: Velvety. Aspect: Hairy, slightly wavy and serrated, slightly shiny. Veins: Upperside: visible; underside: well pronounced, light green, shiny. Color (upperside): Yellow-Green Group 147 A. Color (underside): Between Greyed-Purple Group 186 A and 187 D. Petiole: Strong, purplish brown, hairy.

*Flowers.*—Buds: Bell-shaped, light green with pinkish touch, 5–7 mm just before opening. Sepals: Five (5). Color: Purplish brown. Calyx: Shape: Funnel-shaped. Aspect: Spear-shaped, hairy. Peduncle: Character: Strong upright, hairy. Color: Purplish brown.

*Individual flowers.*—Size: 30–35 mm. Shape: Single violet-shaped. Color (upperside): Purple Group 75 B to C with center being Red-Purple Group 74 B and Purple-Violet Group 80 A. Under cooler temperatures and more intensive lighting, the pink tends to intensify. Color (underside): Purple Group 75 C to D with touches of Purple-Violet Group 81 C. Borne: Each flower stem carries 11–13 and more flowers on strong, upright peduncles that are free standing above the leaves, thereby forming a compact bouquet. Flowering habit: Flowers 9–10 weeks after potting.

*Reproductive organs.*—Stamens: Two (2). Anthers: 2 composed of 4 anther cells, seed capsules push slightly through. Filaments: Yellowish white, 3–4 mm long. Pollen Color: Yellow Group 7 A. Styles: 6–7 mm long, purplish pink, base of ovary light green and hairy.

*Roots.*—Normally developed, white when young, turning slightly brownish when older.

Disease resistance: Up to date, Ilona has shown very good resistance to all major violet diseases.

General Observations

Ilona is an attractive cultivar due to its interesting multicolored flowers which are light pink with a bright pink center radiating into the petals. The center also has some purplish touches. A tight bouquet of flowers free standing above the leaves develops 9–10 weeks after potting. Each of the 8–10 and more strong flower stems carries 11–13 and more small, single violet-shaped flowers, occasionally having 6 petals or an additional very small petal in the center. Medium green, oval to spear-shaped leaves surround the flower bouquet. The flowers are long-lasting and non-dropping and the seed capsules push slightly through.

I claim:

1. A new and distinct cultivar of African violet plant named Ilona, as described and illustrated, and particularly characterized by its small, single violet-shaped, multicolored light pink flowers with bright pink center radiating into the petals and purplish touches in the center; strong, upright flower stems that curve slightly toward the center to form a compact bouquet above the leaves; medium green, oval to spear-shaped leaves; profuse flowering; vigorous and compact growth habit; flowering 9–10 weeks after potting, and its long lasting and non-dropping flowers.

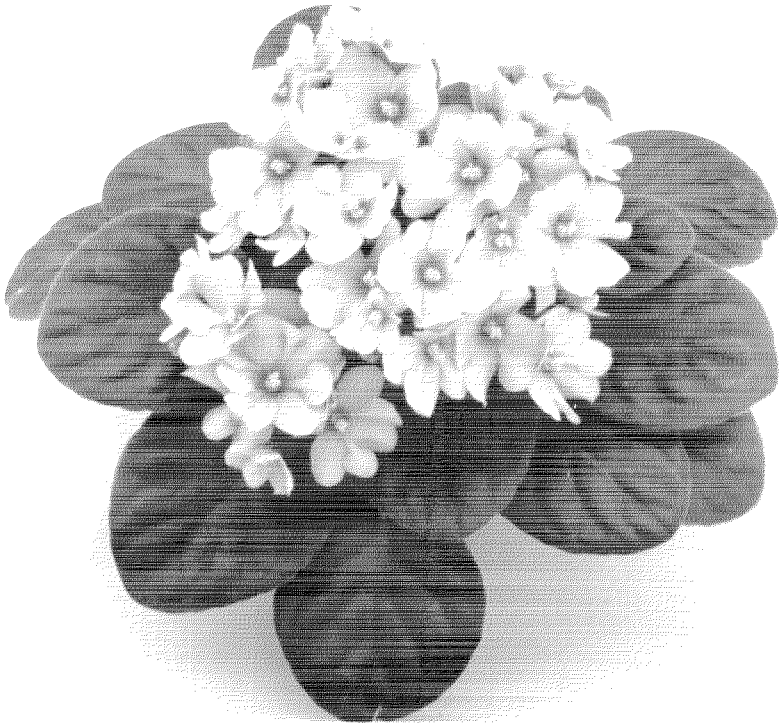

* * * * *